United States Patent
Gravenstein et al.

(10) Patent No.: US 6,322,498 B1
(45) Date of Patent: Nov. 27, 2001

(54) IMAGING SCOPE

(75) Inventors: Dietrich Gravenstein; Samsun Lampotang; Richard Melker; Andrea Gabrielli, all of Gainesville, FL (US)

(73) Assignee: University of Florida, Gainesville, FL (US)

(*) Notice: Subject to any disclaimer, the term of this patent is extended or adjusted under 35 U.S.C. 154(b) by 0 days.

(21) Appl. No.: 09/007,939

(22) Filed: Jan. 16, 1998

Related U.S. Application Data (63) Continuation-in-part of application No. PCT/US97/17954, filed on Oct. 6, 1997, which is a continuation of application No. 08/725,779, filed on Oct. 4, 1996, now Pat. No. 6,115,523.

(51) Int. Cl.[7] ........................................ A61B 1/267
(52) U.S. Cl. ............................ 600/120; 600/130; 600/143
(58) Field of Search .............................. 600/120, 130, 600/114, 143, 121, 144; 606/15

(56) References Cited

U.S. PATENT DOCUMENTS

| | | |
|---|---|---|
| D. 410,286 | 5/1999 | Tamirisa . |
| 3,417,746 | 12/1968 | Moore et al. . |
| 3,776,222 * | 12/1973 | Smiddy ................................ 600/120 |
| 3,913,568 * | 10/1975 | Carpenter ............................ 600/120 |
| 3,941,121 | 3/1976 | Olinger et al. . |
| 4,063,561 | 12/1977 | McKenna . |
| 4,244,362 | 1/1981 | Anderson . |
| 4,475,539 | 10/1984 | Konomura . |
| 4,567,882 | 2/1986 | Heller . |
| 4,607,622 * | 8/1986 | Fritch et al. ........................ 600/109 |
| 4,617,915 | 10/1986 | Arakawa . |
| 4,736,733 | 4/1988 | Adair . |
| 4,742,819 * | 5/1988 | George ................................ 600/120 |
| 4,782,819 * | 11/1988 | Adair ................................... 600/136 |
| 4,800,870 * | 1/1989 | Reid, Jr. ............................... 600/143 |
| 4,846,153 | 7/1989 | Berci . |
| 4,854,301 | 8/1989 | Nakajima . |
| 4,862,258 * | 8/1989 | Kidawara et al. .................. 600/132 |
| 4,924,855 | 5/1990 | Salerno et al. . |
| 4,943,770 | 7/1990 | Ashley-Rollman et al. . |
| 4,980,012 | 12/1990 | Nieda et al. . |
| 5,095,888 * | 3/1992 | Hawley ................................ 600/194 |
| 5,125,406 | 6/1992 | Goldstone et al. . |
| 5,127,079 | 6/1992 | Suzuki et al. . |
| 5,131,380 * | 7/1992 | Heller et al. ........................ 600/121 |
| 5,202,795 | 4/1993 | Kashima . |
| 5,205,280 * | 4/1993 | Dennison, Jr. et al. ............ 600/112 |
| 5,257,636 | 11/1993 | White . |
| 5,279,281 * | 1/1994 | Harvey ................................ 600/164 |
| 5,327,881 * | 7/1994 | Greene ................................ 600/120 |

(List continued on next page.)

FOREIGN PATENT DOCUMENTS

| | | |
|---|---|---|
| 4132687 | 4/1993 | (DE) . |
| 9814112 | 4/1998 | (WO) . |

Primary Examiner—John P. Leubecker
(74) Attorney, Agent, or Firm—Allen, Dyer, Doppelt, Milbrath & Gilchrist, P.A.

(57) ABSTRACT

The subject invention pertains to a system for imaging the human airway having highly advantageous optical, mechanical, ergonomical and physical characteristics. In a specific embodiment, the human airway can be imaged during the intubation procedure. The subject imaging scopes can incorporate a malleable stylet which retains its shape when bent, in order to facilitate intubation of a patient. In a preferred embodiment, a solid metal stylet, for example, a conventional endotracheal tube stylet, can be utilized. In a specific embodiment the subject intubation scope allows for a user to utilize conventional techniques for the insertion of an endotracheal tube, reducing the training needed for use of the subject intubation scope. Preferably, the subject imaging scopes also incorporate at least one illumination fiber to convey light to the distal tip of the subject imaging scopes, for illumination of the objects to be imaged.

4 Claims, 7 Drawing Sheets

U.S. PATENT DOCUMENTS

| | | |
|---|---|---|
| 5,329,940 | 7/1994 | Adair . |
| 5,337,735 | 8/1994 | Salerno . |
| 5,363,838 * | 11/1994 | George ............................... 600/109 |
| 5,377,047 | 12/1994 | Broome et al. . |
| 5,394,865 | 3/1995 | Salerno . |
| 5,402,508 | 3/1995 | O'Rourke et al. . |
| 5,431,152 | 7/1995 | Flam et al. . |
| 5,445,144 | 8/1995 | Wodicka et al. . |
| 5,459,605 | 10/1995 | Kempf . |
| 5,512,034 | 4/1996 | Finn et al. . |
| 5,560,351 | 10/1996 | Gravenstein et al. . |
| 5,606,170 | 2/1997 | Saaski et al. . |
| 5,607,386 * | 3/1997 | Flam .................................. 600/120 |
| 5,676,635 * | 10/1997 | Levin ................................. 600/120 |
| 5,702,345 * | 12/1997 | Wood et al. ........................ 600/132 |
| 5,733,241 * | 3/1998 | King ................................... 600/121 |
| 5,733,242 * | 3/1998 | Rayburn et al. .................... 600/120 |
| 5,735,792 * | 4/1998 | Vanden Hoek et al. ............ 600/138 |
| 5,803,898 | 9/1998 | Bashour . |
| 5,842,973 * | 12/1998 | Bullard ............................... 600/120 |
| 5,846,183 * | 12/1998 | Chilcoat ............................. 600/120 |
| 5,941,818 * | 8/1999 | Hori et al. .......................... 600/143 |

* cited by examiner

IMAGING SCOPE

CROSS REFERENCE TO RELATED APPLICATION

This application is a continuation-in-part of patent application Ser. No. PCT/US97/17954, filed Oct. 6, 1997; which is a continuation of patent application Ser. No. 08/725,779 filed Oct. 4, 1996, now U.S. Pat. No. 6,115,523.

BACKGROUND OF THE INVENTION

This invention relates to fiber optic imaging scopes and, in a particular embodiment, to intubation scopes. The subject intubation scopes can incorporate a malleable stylet, which can retain its shape when bent, to facilitate intubation. Advantageously, this invention can utilize plastic optical fibers to enhance the safety and efficacy of procedures performed with these novel fiber optic scopes, while simultaneously reducing the costs. Additionally, the scopes of the subject invention can, optionally, utilize a sheath which can reduce the amount of cleaning, i.e., sterilization, required between uses and thereby reduce the costs of use.

It is frequently necessary in medical procedures to insert an endotracheal tube into the trachea of a patient for the purpose of performing diagnostic tests or for the introduction of some means of ventilation, oxygenation, and/or airway protection. Even in the best situations, intubation is often difficult and can give rise to complications. In many patients, establishment of the airway is particularly difficult due to morphologic anomalies such as a large tongue, excessive pharyngeal or laryngeal soft tissue, or tracheal displacement, as well as physiologic events such as laryngospasm, regurgitation of gastric materials, bleeding, or foreign bodies aspiration. These morphologic anomalies and/or events make it difficult to visualize the posterior pharyngeal area and larynx with conventional laryngoscopic maneuvers. In emergency situations, attempts to intubate such patients are difficult and time consuming. Inability to expeditiously intubate the patient and protect the airway can lead to significant hypoxemia, myocardial ischemia, and brain injury. Cases of death have also been related to complications caused by the inability to quickly and clearly see the larynx and trachea.

Proper intubation requires positioning the tip of the tracheal tube within the trachea, midway between the patient's vocal cords and carina. Direct laryngoscopy in many instances is sufficient to intubate the patient, but does not permit the precise confirmation of tip location or tracheal inspection.

If the tracheal tube is not inserted far enough past the vocal cords, the tube may become dislodged and prove to be ineffective in supporting adequate artificial ventilation. Further, the tube may inadvertently end up in the esophagus. Esophageal intubations, resulting from either dislodgement or incorrect initial placement have led to severe morbidity and even death. At the other extreme, if inserted too far and beyond the carina, the tube may only permit ventilation of one lung (as opposed to both lungs). Thus, correct tube placement is essential in order to properly ventilate the patient.

Even the most skilled anesthesiologist may encounter what is commonly referred to as a "difficult" airway. This occurs in about 5% of all operating room intubations, with an even higher incidence of an inability to fully visualize the glottic opening. The incidence level is significantly higher in other areas of the hospital and prehospital environment. Although presurgical examination of the jaw, teeth, mouth opening and neck motion assists in gauging the degree of difficulty likely to be encountered at intubation, not all difficult intubations can be identified in advance. There is always the unexpected difficult airway, discovered only at the time of intubation. In emergency situations, there is little if any time to perform an airway assessment prior to attempting intubation. Thus, all emergency intubations are considered "difficult" intubations.

There are a number of techniques used to assist in difficult intubations. These include laryngoscopy, with or without axial cervical stabilization, fiberoptic bronchoscopy, with or without a transtracheal retrograde wire guide, blind nasal and the lighted stylet techniques.

Fiberoptic bronchoscopy is considered by many as the "gold standard" for viewing the airway and properly positioning a tracheal tube. The complexity of operating and cost of buying, maintaining, cleaning, and repairing existing glass fiberoptic systems, which are fragile, are major factors preventing greater usage of bronchoscopy.

The retrograde wire technique involves placing a needle into the cricothyroid space and advancing a guide wire through the needle and upward through the glottic opening between the vocal cords and pharynx until it emerges from the nose or mouth. After the wire is localized, a fiberoptic bronchoscope or tracheal tube is advanced over the wire into the larynx. This technique is not recommended in emergency situations. Major negative concerns associated with this technique are its invasive nature and the risk for bleeding and infection in the trachea. The wire can also cause injury to the tracheal tissue and/or vocal cords.

A lighted stylet is essentially a standard stylet with a bright light at the distal end. This technique provides only indirect transcutaneous illumination of the trachea. Direct visualization is not possible when using a lighted stylet.

Fiberoptic intubating scopes with cameras and/or eyepieces for viewing that which is illuminated by the fiber optic system have previously been described. See, for example, U.S. Pat. Nos. 3,776,222; 4,742,819; 4,846,153 and 5,363,838. Current fiber optic scopes, for example, intubation scopes and associated systems for imaging the human airways, typically use glass optical fibers. Unfortunately, these intubation scopes and associated systems utilizing glass optical fibers are expensive to purchase, clean, and store. Additionally, the glass optical fibers within these scopes are prone to breaking thereby shortening the life of the scopes.

BRIEF DESCRIPTION OF THE INVENTION

The subject invention pertains to a system for imaging the human airway having highly advantageous optical, mechanical, ergonomical and physical characteristics. The subject system allows for a user to utilize conventional techniques for the insertion of an endotracheal tube while using the subject imaging scope. The excellent characteristics of the imaging system of the subject invention result, in part, from the use of plastic optical fibers. Plastic optical fibers are more robust than the glass optical fibers used in currently available imaging systems, and are therefore capable of being bent and/or twisted with virtually no concern of breakage. In addition, the lower costs of plastic optical fibers enables scopes of the subject invention, in a specific embodiment, to be manufactured for single patient use thereby eliminating the requirement for cleaning, special care, the maintenance of expensive inventory, and most importantly eliminating the opportunity for cross contamination between patients. A further aspect of the subject invention concerns a novel sheath which can cover all or a portion of the parts of the imaging system which enter the patient. This sheath can reduce the need for expensive sterilization of the subject intubation scope after use.

An embodiment of the subject imaging system utilizing plastic optical fiber is highly advantageous because of its longer life, increased ruggedness, greater flexibility, comparable image quality, optional disposability, and lower cost, compared to glass scopes. These scopes are useful, for example, for observing the bronchi of the lungs, locating the tracheal opening to allow insertion of an endotracheal tube into the trachea for intubation, and visually locating the endotracheal tube tip. Specifically, using a scope of the subject invention, a practitioner can easily and precisely identify the exact location of the distal end of the tracheal tube, as well as the various anatomical airway landmarks. Currently, this degree of precision is only possible with an expensive glass fiberoptic bronchoscope. In addition, the scopes of this invention are particularly advantageous for use in anesthesiology.

In a specific embodiment, the subject imaging system can incorporate a malleable stylet which can retain its shape when bent. This embodiment can be used as an intubation scope. During an intubation, an anesthesiologist can insert the subject intubation scope into an endotracheal tube to be inserted into a patient. Once the intubation scope is inserted into the endotracheal tube, the anesthesiologist can bend the intubation scope—endotracheal tube combination into a shape, essentially any shape, which facilitates insertion into the patient. Advantageously, the anesthesiologist can then hold the scope-tube combination in one hand, with a conventional grip, for example in a pen-like fashion, and easily maneuver the scope-tube combination during insertion into the patient.

While prior art scopes have required the anesthesiologist to change the standard procedure for inserting an endotracheal tube, for example by holding on to the scope and/or manipulating a handle on the scope to direct the tip of the scope, an anesthesiologist using the subject scope can hold the endotracheal tube in the conventional manner during intubation. This is an important improvement over the prior art because anaesthesiologists are not necessarily trained in endoscopy and without such additional training, would not normally be adept with the techniques for use of such prior scopes. The subject technology can therefore be referred to as a transparent technology, due to the minimal instruction needed before use thereof. Specifically, the subject invention allows an anaesthesiologist to hold the scope-tube combination with one hand during intubation and, for example, use a laryngoscope with the other hand, if necessary. In addition, the subject intubation scopes can be removed from the endotracheal tube, after insertion, with only one hand, thus freeing the anaesthesiologist3 s other hand. This is in contrast to many prior art scopes which require two hands for use, for example due to a twist motion needed to unlock the scope from the endotracheal tube.

In a specific embodiment, the subject invention pertains to a plastic optical fiber imaging scope, having an optional sheath, for intubation. This intubation scope can be used for intubation of patients under general and/or local anesthesia. The intubation scope of this embodiment can be disposable, sterilizable for reuse, or enclosed within a disposable sheath for reuse without expensive sterilization. Due to lower cost for the plastic optical fiber scopes, the scopes of the subject invention are particularly advantageous for situations calling for disposable scopes, and can be less expensive than the cleaning and sterilization costs for existing glass scopes.

Imaging scopes with varying components and corresponding performance capabilities can be manufactured with this new technology. By way of these multiple embodiments, the subject invention can be used for imaging essentially all of the airway system of humans and animals.

DETAILED DESCRIPTION OF THE INVENTION

The subject invention utilizes optical fiber to produce fiber optic scopes, and in a particular embodiment, intubation scopes, for use in imaging the human airway. In a preferred embodiment, the subject invention utilizes plastic optical fiber. The device of the subject invention can assist practitioners in properly introducing and confirming the position of tracheal tubes. Although the device has application in "difficult" intubations, use in all intubations is envisioned for confirming optimal tracheal tube advancement between the vocal cords and positioning within the trachea. This can only be achieved with direct tracheal visualization. The plastic fiberoptic device of the subject invention makes this possible while also being highly cost effective.

The device of the subject invention has application for intubating patients undergoing general, intravenous and local anesthesia and in emergency situations. Thus, the device can be used in surgical procedures as well as in intensive care units, emergency departments and the prehospital settings.

The device of the subject invention can incorporate plastic fiberoptic technologies, enabling direct visualization of the pharynx, glottic opening, larynx and trachea and thus, facilitate accurate tracheal tube placement and periodic verification of tracheal tube tip location. Further, the subject device can easily be steered, simplifying proper tube placement. Traditional reusable glass fiber bronchoscopes are expensive to purchase and maintain. Effectively cleaning the bronchoscope is difficult. It is also recognized that sterility of existing reusable glass fiber bronchoscopes is often not achieved after use with a patient.

The subject invention achieves substantial improvements in performance compared to existing glass fiber scopes, including: (1) longer life; (2) increased ruggedness; (3) greater flexibility; (4) optional disposability; (5) greater ease of use; and (6) less expense. By varying the components of the intubation scopes utilizing the teachings of the subject invention, these performance characteristics can be optimized, to facilitate the use of these scopes for imaging a vast portion of the human airways and in a variety of situations. Thus, the scopes of the subject invention can be used, for example, for observing the bronchi of the lungs, locating the tracheal opening to allow insertion of an endotracheal tube into the trachea for intubation, and locating the endotracheal tube tip. In particular, an anesthesiologist can, using the scope of the subject invention, stand behind the head of a patient while performing an intubation. Additionally, this device will reduce the force necessary for laryngoscopy. Reduced force leads to less tissue trauma, hemodynamic changes, and post-operative sore throat complications. Advantageously, the scopes of the subject invention are more cost effective in situations requiring a disposable scope and/or can be used with an optional disposable sheath to enclose the portion of the scope entering the body to reduce cleaning and sterilization costs.

In one embodiment the light source can be derived from a standard laryngoscope. In a second embodiment, one or more optical fiber(s) can transmit the light required to illuminate the airway. The source of the light can be, for example, a laryngoscope or an inexpensive separate light source.

Image guides used in conjunction with intubation, for example, bronchoscopes, are typically made with step index glass optical fiber. Plastic optical fiber can also be fabricated with a step index of refraction. Both plastic and glass step index fibers are constructed with a core of refractive index $n_1$, and a cladding of refractive index $n_2$, where $n_1 > n_2$. A second type of fiber is known as gradient index or graded index fiber and can also be made with plastic or glass. Since flexibility is an important characteristic for the scopes of the subject invention, plastic gradient index optical fibers are preferred over glass gradient index optical fibers for the subject image guides.

In comparing the step index structure with the gradient index structure, it is noted that there are different trajectories of light rays in these two fiber structures. Within step index fiber, the light travels in straight lines, and is reflected at the core-cladding interface. While in gradient index fiber, the light travels in a curved trajectory always being refracted back towards the axis of the fiber. As a consequence, an image can be conveyed within a single gradient index fiber, while an image cannot be conveyed within a single step index fiber. Although, when conveying an image in a single gradient index fiber, some correction may be required to correct aberrations in the output image, for example, by using one or more negative gradient index lens attached to one or both ends of the single gradient index fiber.

Figure 1:
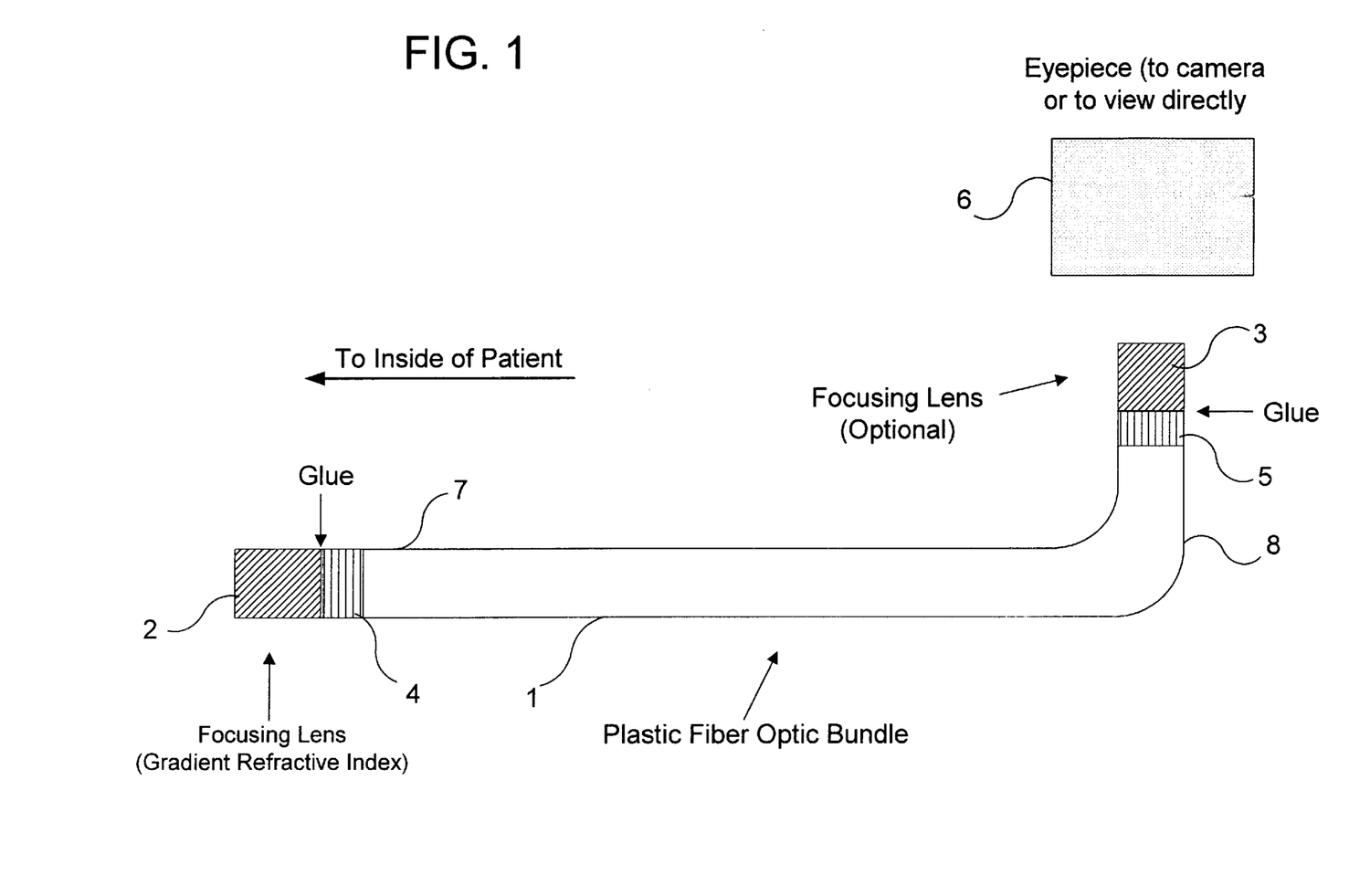
FIG. 1 shows an embodiment of the intubation scope of the subject invention.

Referring to FIG. 1, the intubation scope of the subject invention comprises an image guide 1, which conveys optical images from inside the body, for example from inside the human airways, to outside of the body for viewing by a medical caregiver. In a specific embodiment, this image guide 1 can comprise a single gradient index plastic optical fiber. In a specific embodiment, this single fiber can have a diameter, for example, of about 0.5 to 2.0 mm. A focusing lens 2 can optionally be used to focus the desired image into the distal tip 7 of the single fiber, the distal tip 7 entering the body, generally through the mouth or nose. This lens 2 can be attached by, for example, optical glue, and can act as a bi-convex lens to focus the desired image onto the distal tip of the single fiber. In this single fiber embodiment, a negative gradient rod lens, made of glass or plastic, can be attached to the proximal end of the single fiber image guide 1 and used to correct for aberrations resulting from the use of a single gradient index plastic optical fiber to carry the image.

In an alternative embodiment, this image guide 1 can comprise a bundle of plastic optical fibers. This plastic fiber optic image guide 1 can be made of a plurality of individual plastic optical fibers which have been fused together. In a specific embodiment, this bundle can comprise approximately 10,000 individual plastic optical fibers, wherein the bundle is approximately 1.0 millimeter in diameter. This bundle can comprise gradient index plastic optical fibers and, in a preferred embodiment, this bundle can comprise step-index plastic optical fibers. Each end of the bundle can be polished to allow high resolution imaging. A focusing lens 2 can be used to focus the desired image onto the distal tip 7 of the bundle, the distal tip 7 entering the human body, generally through the mouth or nose. This lens 2 can be attached at the distal tip 7 of the bundle, for example, by optical glue 4. This lens 2 can act like a bi-convex lens to focus the image onto the distal tip of the fiber optic bundle. In a preferred embodiment, the lens 2 can be a gradient-index glass rod lens. In a more preferred embodiment, the lens 2 can be a gradient-index plastic rod lens.

An optical system can transmit the image from the proximal end of the fiberoptic image guide 1 onto a charge coupled device (CCD). The CCD can be used to convert the image into an electrical signal which can be displayed on a monitor. Alternatively, camera equipment available to the physician can be used. In a specific embodiment, the proximal tip 8 of the image guide 1 is arranged so that the image from inside the patient is focused directly onto an imaging eyepiece 6. The imaging eyepiece 6 can be connected to a camera for viewing the image, or the image can be viewed directly by the medical caregiver through the imaging eyepiece 6.

In an alternative embodiment, when a camera is not to be used for viewing the image, a second lens 3 can be attached, for example, by optical glue 5, to the proximal tip 8 of the image guide 1, the proximal tip remaining outside of the body. This lens can be, for example, a mini plastic lens microscope connected directly to the proximal end of the fiber scope for direct viewing by the caregiver, i.e., by placing an eye to the microscope lens. In a specific embodiment, the fiberoptic image guide can be lengthened and mini plastic lens microscope can be mounted on a caregiver's head, for example, by a mounting means such as a pair of glasses or goggles. This allows the caregiver to have both hands free to perform, for example, an intubation, while being able to view the patient and the image from the scope without having to turn his or her head.

Manufacturing the subject invention without a camera can be done to reduce costs or to meet the needs of certain medical situations. However, when the eyepiece is connected to a camera, the image can be displayed via, for example, a television monitor. This monitor can be, for example, placed out of the sterile field for viewing.

In a specific embodiment, the visualization system scope of the subject invention can be inserted into a plastic tube (sheath), which can have a transparent end plate. This combination can then be used for imaging the airway. The image viewed through the end plate is unimpaired by the sheath or end plate. The advantage of this sheath is that it is disposable and allows the intubation scope to be reused with minimal sterilization.

Figures 2A, 2B:
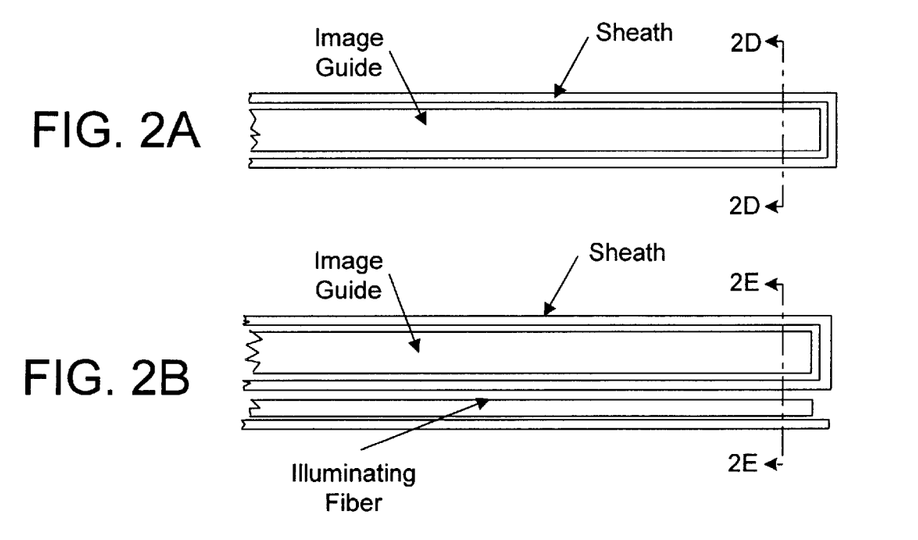
FIGS. 2A and 2D illustrate a longitudinal cross section and a transverse cross section, respectively, of the distal end of a sheath designed to fit over a plastic optical fiber image guide.
FIGS. 2B and 2E illustrate a longitudinal cross section and a transverse cross section, respectively, of the distal end of a sheath designed to fit over a plastic optical fiber image guide, wherein the sheath comprises an illumination fiber.
Figure 2C:
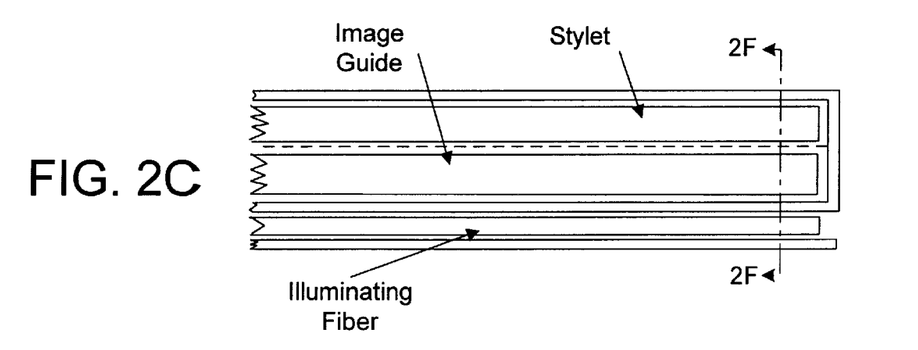
FIGS. 2C and 2F illustrate a longitudinal cross section and a transverse cross section, respectively, of the distal end of a sheath designed to fit over a stylet incorporated with a plastic optical fiber image guide, wherein the sheath comprises an illumination fiber.

In a preferred embodiment, the sheath can have at least one internal, or external, illuminating optical fiber(s) which transmits light to illuminate the internal body structure to be imaged. Additionally, it is preferred but not essential, that there be no transparent end plate at the distal end of the illuminating optical fiber(s) to avoid the illuminating light reflecting at such a plate and impairing the quality of the image. A longitudinal cross section and a transverse cross section of a sheath comprising an external illumination fiber are shown in FIGS. 2B and 2E, respectively.

When performing, for example, an intubation, a malleable stylet, typically made of metal, is often used in conjunction with an endotracheal tube to facilitate the placement of the tube into the body. In a specific embodiment, the subject intubation scope can incorporate a stylet, wherein the stylet can be bent into the shape which the caregiver believes will facilitate the easiest and safest placement of the endotracheal tube, and then the endotracheal tube, which typically surrounds the stylet and scope, can be inserted into the patient. A longitudinal cross section and a transverse cross section of a sheath comprising an external illumination fiber, where the sheath is designed to fit over a stylet incorporated with a plastic optical fiber image guide, are shown in FIGS. 2C and 2F, respectively. In this case, the sheath and illuminating fiber could be regarded as disposable after a single use.

Accordingly, the intubation scope and/or sheath of the subject invention can comprise such a stylet, such that many combinations of scope, stylet, illuminating fiber(s), and sheath are possible. In accordance with the subject invention, the combination of an image guide and a malleable stylet, which retains its shape when bent, facilitates the placement of an endotracheal tube into a patient. In a preferred embodiment, a solid metal stylet, for example a conventional endotracheal tube stylet, can be utilized. The image guide can be attached to the stylet such that the image guide takes essentially the same shape as the stylet when the stylet is bent. In a specific embodiment, referring to FIG. 6, the image guide can be incorporated into the stylet. Accordingly, the stylet-image guide combination, i.e., the intubation scope, can be inserted into an endotracheal tube which is to be inserted into a patient. In a more preferable embodiment, the intubation scope can also comprise an illumination fiber, for example also attached to the stylet.

Once the intubation scope is inserted into the endotracheal tube, a caregiver can bend the endotracheal tube into the shape, essentially any shape, which the caregiver believes will facilitate the easiest and safest insertion of the endotracheal tube. In fact, a caregiver can insert the tube-scope combination into a patient using one hand to hold and maneuver the tube-scope combination. Once the tube-scope combination is in place in the patient, a caregiver can, again with one hand, remove the subject intubation scope from the endotracheal tube.

A variety of attachment means can be utilized in accordance with the subject invention to attach the stylet, image guide, and/or illuminating fiber. It is preferred that the relative position of the distal tip of the image guide and the distal tip of the illumination fiber remain fixed, both in angular orientation and axial translation, in order to enhance the quality of the image. In addition, it is preferred that the relative position of the distal end of the stylet also remain fixed with respect to the distal tip of the image guide.

Figures 4A, 4D:
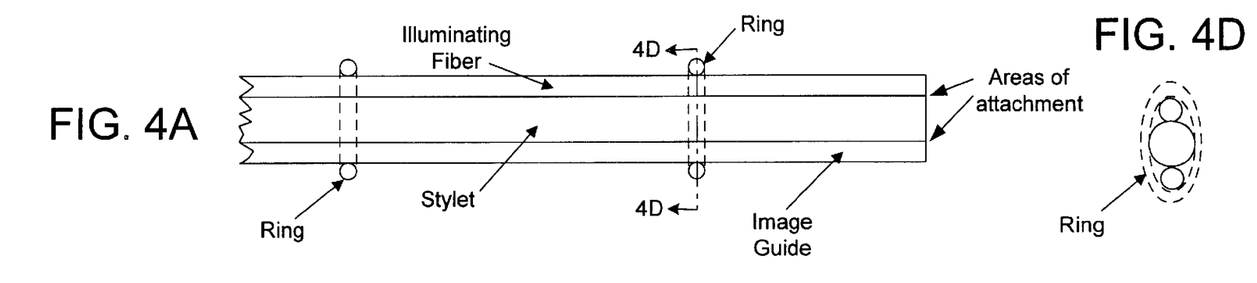
FIGS. 4A and 4D illustrate a longitudinal cross section and a transverse cross section, respectively, of the distal end of an embodiment of the subject invention comprising a stylet, an image guide, at least one illumination fiber, and rings to hold the components together.

Referring to FIGS. 4A and 4D, a specific embodiment of the subject invention is shown where the distal ends of a stylet, an image guide, and an illumination fiber are securely attached to each other via an attachment means, for example with glue or a clip. This embodiment also includes rings, for example made of an appropriate elastic material, which hold the various components together along the length of the intubation scope. These rings can allow for slippage of the various components, for example during the bending of the intubation scope, while maintaining the relative positions of the distal ends of the various components.

Figure 4B:
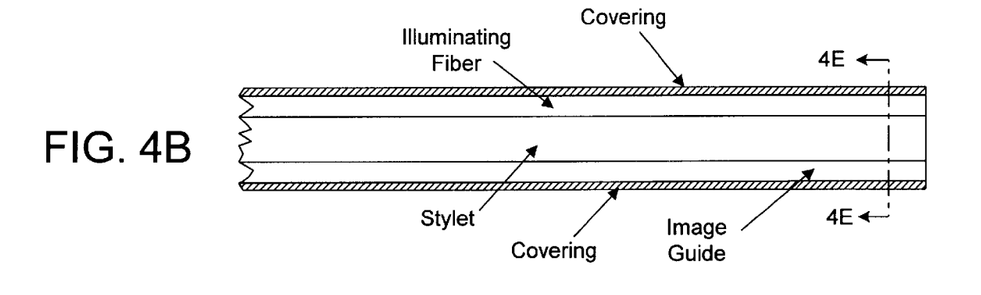
FIGS. 4B and 4E illustrate a longitudinal cross section and a transverse cross section, respectively, of the distal end of an embodiment of the subject invention comprising a stylet, an image guide, at least one illumination fiber, and an outer covering to hold the components together.
Figure 4C:
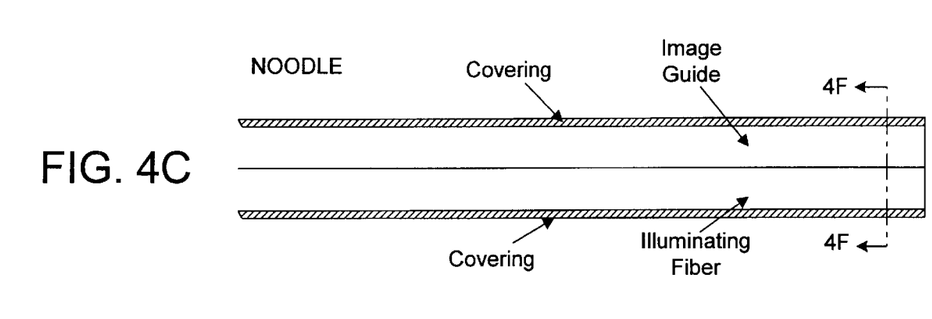
FIGS. 4C and 4F illustrate a longitudinal cross section and a transverse cross section, respectively, of the distal end of a flexible embodiment of the subject invention comprising an image guide, at least one illumination fiber, and an outer covering to hold the components together.
Figure 4E:
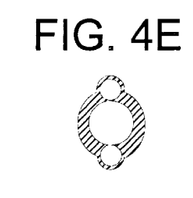

Alternatively, referring to FIGS. 4B and 4E, an outer covering can be used to hold the various components together. This outer covering can be made of a material, for example a polymer, which can alter, either increase or reduce, the friction between the subject intubation scope and the inside of an endotracheal tube. For example, reduced friction can facilitate the removal of the subject intubation scope after intubation of a patient. Again, it is preferred that the relative positions of the distal ends of the various components remain constant. In an additional embodiment, a transparent end covering can be utilized to cover the distal tip of the intubation scope.

Figure 4F:
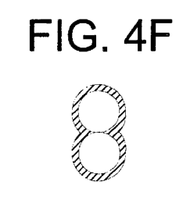

FIGS. 4C and 4F show an embodiment of the subject invention which can be referred to as a noodle. This embodiment does not incorporate a stylet and, therefore, can be useful, for example, for nasal intubations. This embodiment can also be used, for example, to check the position of the distal tip of an endotracheal tube which is in place in a patient.

Stylets of various cross-sectional shapes can be used in accordance with the subject invention. A variety of materials for producing the stylet are also envisioned within the scope of the subject invention, for example polymers, metals, or other materials having the proper physical characteristics. It is important for the stylet to be malleable such that the stylet can be bent and will retain its shape when bent. Preferably, the subject stylet can be bent easily by a user into essentially any shape which will facilitate the insertion.

Figure 5:
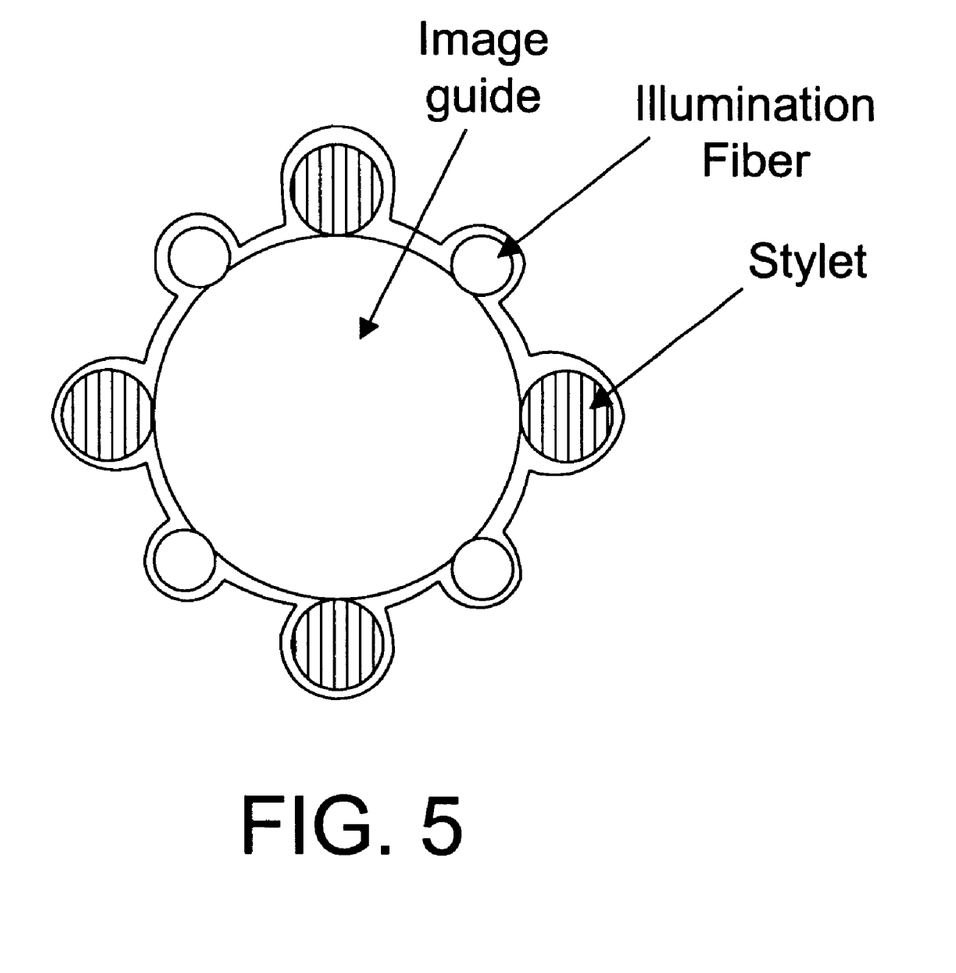
FIG. 5 illustrates a specific embodiment of the subject invention comprising an image guide, at least one illumination fiber, and a stylet made of multiple wire strands.

In addition, the subject intubation scopes can have a coating, for example a polymer coating. In a specific embodiment, this coating can be placed around a solid cylindrical rod made of a malleable metal. The coating can be used to modify friction between the endotracheal tube and the subject scope so as to optimize movement of the scope within the tube. For example, a low friction coating may decrease friction between the scope and the endotracheal tube so as to ease withdrawal of the scope from the tube. Various cross-sectional shapes for the subject intubation scopes are also possible. For example, referring to FIG. 5, the subject scope can incorporate a stylet comprising multiple, thinner rods which can be positioned circumferentially around the image guide. If illumination fibers are utilized, these illumination fibers can also be positioned circumferentially around the image guide, for example interspaced with the multiple rods of the stylet. In addition, a coating and/or an outer covering can be applied to the outside of the intubation scope to assist in holding the multiple stylets and multiple illumination fibers to the side of the image guide. This coating may allow for reuse of the subject scope, for example after cleaning.

Figure 6:
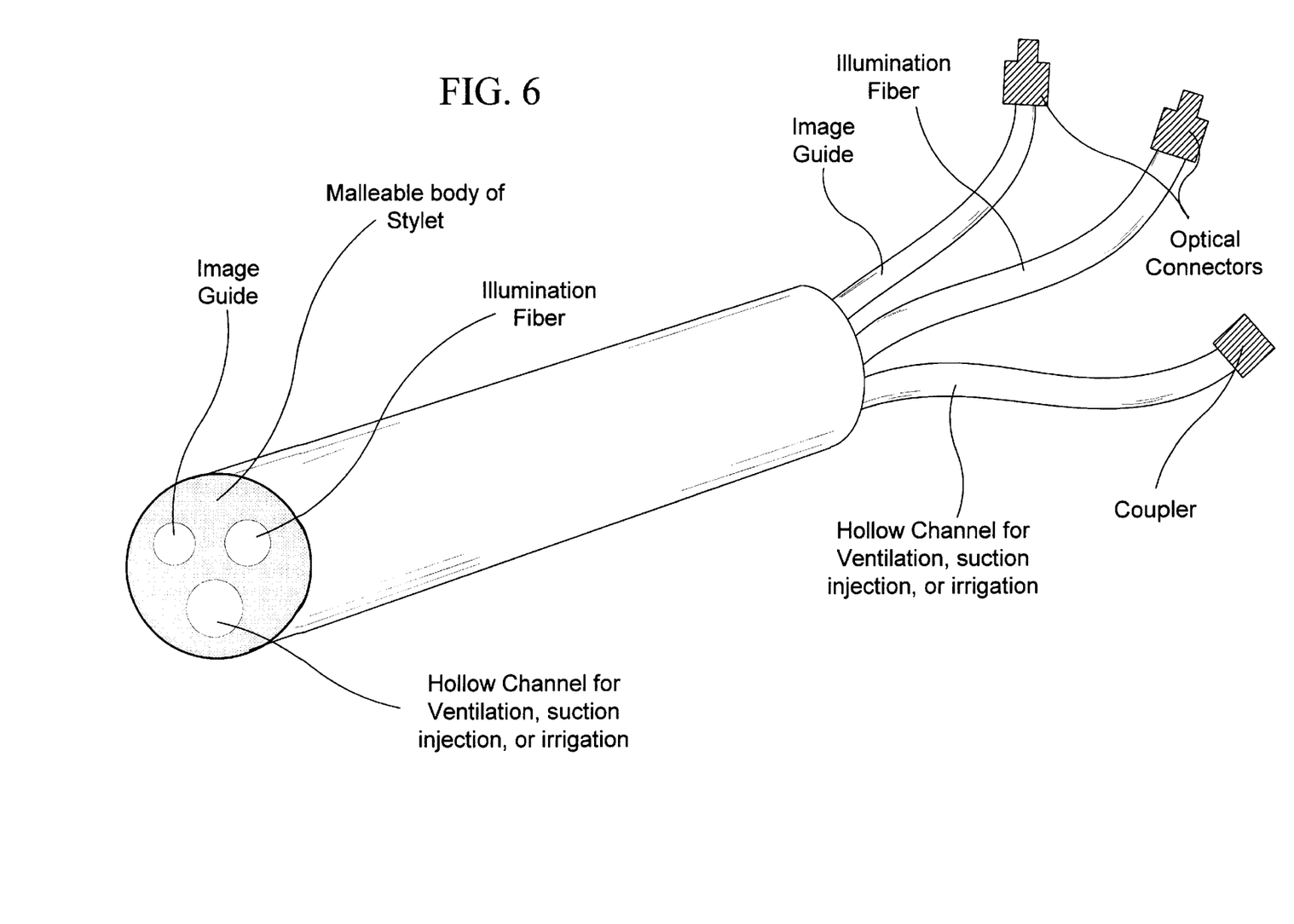
FIG. 6 illustrates an embodiment of the subject invention wherein an image guide, an illumination fiber(s), and a hollow channel are housed within a malleable stylet.

In an additional embodiment, referring to FIG. 6, an outer covering around the subject image guide can act as a stylet, for example if the outer coating is malleable and retains its shape when bent. The embodiment shown in FIG. 6 comprises a malleable stylet having hollow channels where an image guide and illumination fiber(s) can reside. This stylet can, for example, be extruded such as to have these channels. As also shown in FIG. 6, an additional channel can be provided for injection, ventilation, suction, and/or irrigation. In a preferred embodiment, the subject imaging scopes have no moving parts other than that resulting from bending of the stylet, image guide, any illumination fibers, and other lumens.

Preferably, during insertion of an endotracheal tube into a patient, the distal tip of the image guide can reside near the distal tip of the endotracheal tube such that a caregiver receives images from near the distal tip of the endotracheal tube, so as to facilitate proper placement of the tube. In addition, it is preferable that the distal tip of the stylet and image guide do not extend from the distal tip of the tube where they may injure the trachea or other areas during the insertion of the tube. To prevent the distal tips of the stylet and image guide from traveling past the distal tip of the tube, the stylet can be bent near the proximal end of the tube, for example bent over the proximal end of the tube. The image guide can be bent as well, for example if attached to the stylet of the scope at the proximal end of the tube, or can move independently from the stylet.

Figure 7:
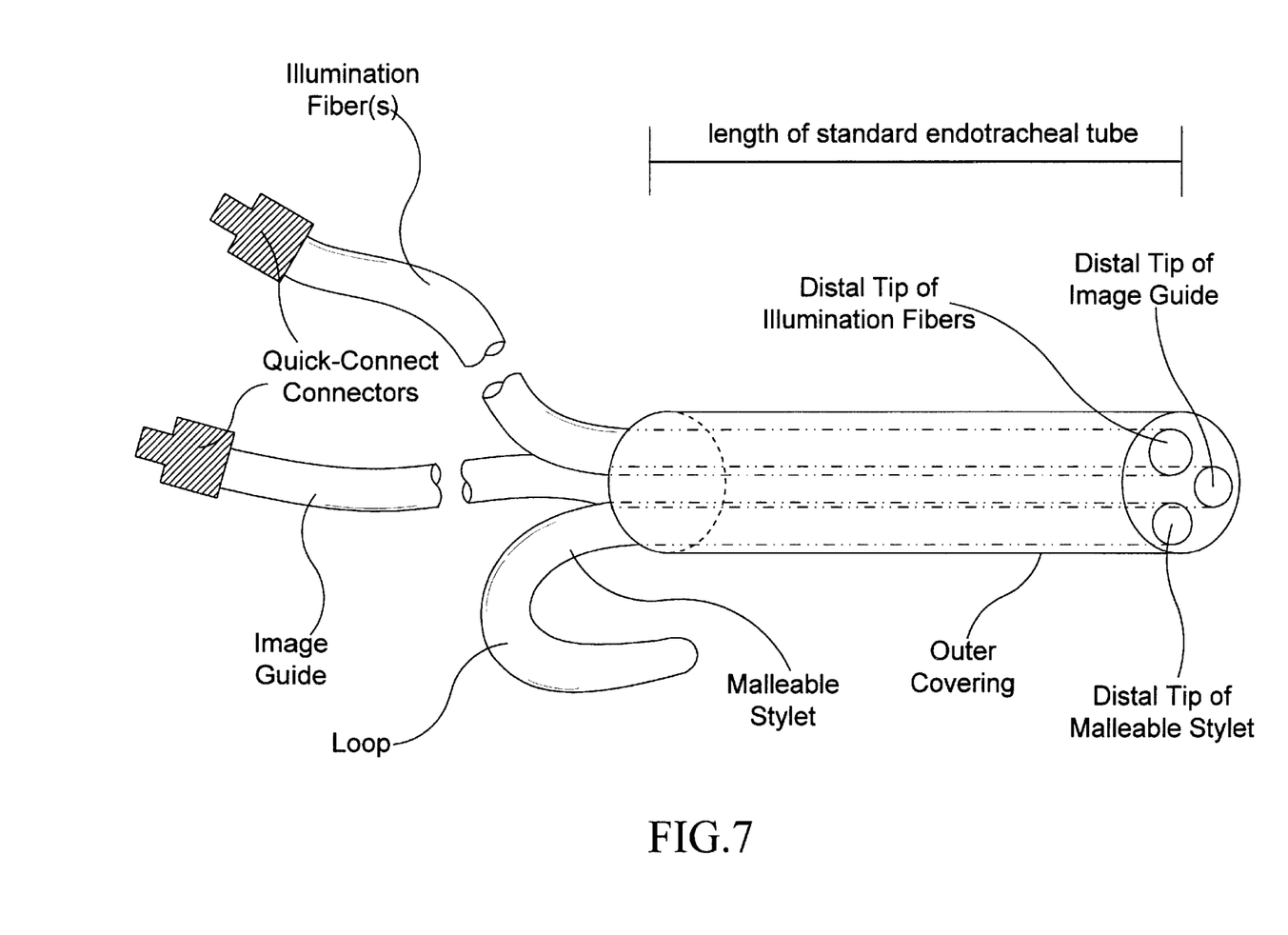
FIG. 7 illustrates a preferred embodiment of the subject invention incorporating an image guide, an illumination fiber(s), and a malleable stylet, held together by an outer covering.

In a preferred embodiment of an intubation scope in accordance with the subject invention, as illustrated in FIG. 7, the proximal end of the stylet can terminate, for example in a loop, at a length slightly longer than an endotracheal tube into which it is to be inserted. Such a loop can allow a caregiver to easily grasp the stylet end to bend the stylet end over the proximal end of the tube. In addition, a looped proximal end of the stylet can assist in removal of the scope from the tube. For example, a user can hold the end of the tube with one hand and use the thumb on the same hand to move the scope out of the tube by hooking the loop with the thumb. Advantageously, due to the lightweight image guide and illumination fiber(s), the center of gravity of the endotracheal tube—intubation scope combination can be located in essentially the same location along the endotracheal tube as with a conventional stylet inserted in an endotracheal tube, such as to provide good balance in the user's hand during intubation. This allows the center of balance of the tube-scope combination in a user's hand to remain in essentially the same position as for a conventional endotracheal tube-stylet combination.

In accordance with the subject invention, the ability of a caregiver to hold the endotracheal tube itself during insertion into a patient has many advantages. By holding the tube with a conventional, or pen-like, grip a caregiver can twist or rotate the tube, as well as move it translationally, with more leverage than if held by, for example, a scope inserted into the tube. During the insertion, a caregiver can view the image from the image guide on, for example, a monitor, without the need to view the patient directly.

In addition, the ability to bend the scope-tube combination in essentially any shape prior to insertion of the tube into a patient can reduce the risk of injury to a patient whose anatomy may require a tailored bend. Advantageously, insertion of the tube can then be performed on a patient in the neutral position. Prior art devices have required the patient to be in a "sniffing" position or to have the head tilted back to create a straighter insertion channel, due in part to the stiffness and limited range of motion of the prior devices. Insertion of the tube while a patient is in the neutral position, as opposed to the sniffing or head-tilted-back positions, results in reduced increases in blood pressure, heart rate, and reduced injury to the treachea. In addition, the ability to bend the scope-tube combination in essentially any shape allows the tube to be preformed to a shape tailored specifically to a patient, prior to insertion of the tube. This allows insertion of the scope-tube combination while a patient is in the neutral position, and can thus eliminate the need for a laryngoscope to elevate tissues. If preferred, a laryngoscope can be used to move the tongue out of the way such that the tube-scope combination can be inserted. However, there is no need to use the laryngoscope to further elevate tissues, for example to see the larynx. The subject tube-scope is preferably rigid enough so that a laryngoscope is not necessary. The scope can sweep the tongue away, eliminating the need for a laryngoscope, thus reducing complications, such as chipped teeth. In addition, less force can be applied, reducing injuries. This allows intubation to be performed while a patient is awake or asleep, in an elective or emergency situation. In addition, the ability to intubate a patient in the neutral position can prevent further injury to a patient with, for example, known or possible neck or spine injuries. Patients with known or possible cervical spine instability or fused/fixed spine can be intubated and/or examined without having to be moved.

In a specific embodiment in accordance with the subject invention, an intubation scope can have a removable stylet. The stylet can be removed to perform, for example, nasal intubation or stoma/tracheotomy. In addition, this embodiment can allow for insertion of an endotracheal tube, utilizing the intubation scope with the stylet attached, and the subsequent verification of the tube's position, utilizing the intubation scope with the stylet removed. In another embodiment, the subject scope can have no stylet. This embodiment can be useful for confirmation of the endotracheal tube location and inspection of patients' tissues and structures, for example to reduce the need for x-rays. FIGS. 4C and 4F illustrate one such embodiment.

In a specific embodiment of the subject intubation scope, a charge-coupled device (CCD) can be mounted at the distal tip of the stylet, which can eliminate the necessity for an optical fiber image guide. The signal generated from the CCD can be carried, for example via wires, to a camera external to the endotracheal tube. This camera can be located in any position which allows a caregiver to conveniently view the camera during intubation of the patient. In a further embodiment, the CCD and camera can be located at the proximal end of the stylet, such that an image is carried from the distal tip of the endotracheal tube to the CCD by an image guide during intubation.

Once the subject intubation scope is inserted into an endotracheal tube and secured in place, for example by bending the proximal end of the stylet over the proximal end of the endotracheal tube, the image carried from the distal tip of the image guide to the proximal end of the image guide needs to be viewed by the caregiver. In a preferred embodiment, the proximal end of the image guide can terminate with a quick-connect connector such that the proximal end of the image guide can easily plug into a device for receiving and displaying the image. Quick-connect connectors are particularly advantageous when a plastic optical fiber image guide and plastic optical fiber illumination fibers are utilized, due to greater misalignment tolerances than with glass optical fiber. The proximal end of any illumination fibers can also terminate with quick-connect connectors such that easy connection to an illuminating light source is possible. In a specific embodiment, slide and lock quick-connect connectors may be utilized. The use of quick-connect connectors allows for a free flexible tail and a lightweight intubation scope. The use of slide and lock quick-connect connectors can assist a caregiver in maintaining proper orientation of the image being viewed and prevent the connector from coming loose during operation, thus enhancing performance.

A preferred embodiment of an intubation scope in accordance with the subject invention is illustrated in FIG. 7. The proximal ends of the illumination fiber and image guide can form a free flexible tail which is lightweight. Accordingly, after insertion of the subject intubation scope into an endotracheal tube, the scope-tube combination can be maneuvered easily and has the same feel in a user's hand as the conventional tube with a conventional stylet inserted. The quick-connect connectors can be connected just before placement of the scope-tube combination into the patient, allowing the caregiver considerable freedom of maneuverability while inserting the intubation scope into the endotracheal tube.

The intubation scope and method of tracheal tube placement verification of the subject invention represents a significant cost saving for the hospital. Rather than having to periodically x-ray the patient to verify tube position, the hospital staff can use the subject invention to not only confirm proper tube placement but to also evaluate the airway for obstruction and/or erosion, which is not possible with x-rays. Advantageously, the use of the subject technology can reduce a patients exposure to x-rays.

The device of the subject invention is easily connected to bronchoscope imaging equipment, without incurring the cost of buying and sterilization processing of the bronchoscope. In another embodiment, an off the shelf LCD device similar to a Sony "WATCHMAN" can be utilized for imaging.

Following are examples which illustrate procedures for practicing the invention. These examples should not be construed as limiting.

EXAMPLE 1

The device of the subject invention not only makes intubation easier and more accurate, but also reduces the potential for inflicting injury with the laryngoscope blade. Using the device of the subject invention, the practitioner only needs to use the laryngoscope blade to control the position of the patient's tongue. The device can also be used without a laryngoscope and for nasotracheal intubation.

The device of the subject invention can comprise a bundle of 10,000 individual plastic optical fibers (bundle is approximately 1.0 millimeter in diameter). The resolution of the image is comparable to an existing glass fiberoptic bronchoscope, providing good visualization of the patient's airway.

The manufacturing process places the bundle integral to a standard malleable stylet. An additional fiber may be used for illuminating purposes. Suctioning and insufflation can be added by adding an additional channel if desired.

A focusing lens (i.e., gradient refractive index lens) is placed at the distal tip of the optical fibers and acts like a bi-convex lens to focus the image onto the distal tip of the fiber optic bundle. An optical system transmits the image from the proximal end of the fiberoptic bundle onto a charge coupled device (CCD). The CCD is used to convert the image into an electrical signal which can be displayed on a monitor. Alternatively, camera equipment available to the physician may be used.

EXAMPLE 2

Figure 2D:
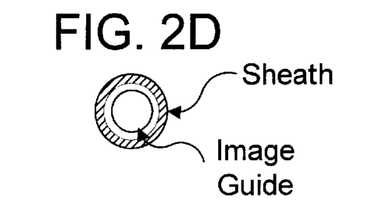
Figure 2E:
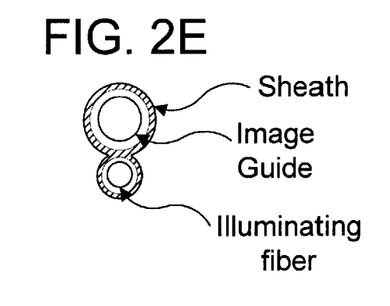
Figure 2F:
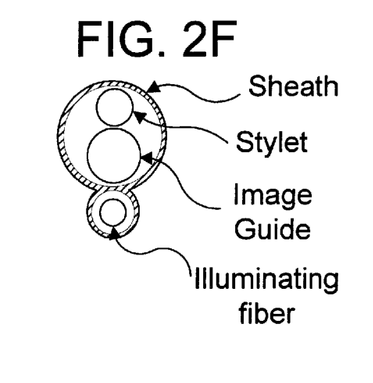

Referring to FIGS. 2A, 2B, 2C, 2D, 2E, and 2F, this example provides three illustrative combinations of image guide, illuminating fiber, stylet, and/or sheath. FIGS. 2A and 2D illustrate a longitudinal cross section and a transverse cross section, respectively, of the distal end of a sheath designed to fit over a plastic optical fiber image guide. The sheath covers the distal tip of the image guide with a transparent end plate. In this case, any illuminating fibers and/or stylets would not be enclosed within this sheath, although they could have their own sheaths.

FIG. 2B and 2E illustrate a longitudinal cross section and a transverse cross section, respectively, of the distal end of a sheath designed to fit over a plastic optical fiber image guide, wherein the sheath comprises an illumination fiber. The distal end of the illumination fiber is not covered by the sheath, in this example, so as to not impair the image. Accordingly, the illuminating fiber can be disposed of with the sheath. In this embodiment, the sheath acts to attach and position the illumination fiber with respect to the image guide.

FIGS. 2C and 2F illustrate a longitudinal cross section and a transverse cross section, respectively, of the distal end of a sheath designed to fit over a stylet incorporated with a plastic optical fiber image guide, wherein the sheath comprises an illumination fiber. The distal end of the illumination fiber is not covered by the sheath, but the distal end of the image guide plus stylet is covered. In this embodiment, the stylet can be reused along with the image guide. Other geometrical arrangements of the stylet, image guide, and illumination fiber are obviously possible.

EXAMPLE 3

It is sometimes necessary to replace an endotracheal tube in a patient, for example when the tube no longer provides an adequate airway. In a specific embodiment, the subject invention can permit the easy removal of one endotracheal tube and its replacement with a new one.

A device in accordance with the subject invention can be inserted into the patient's trachea, generally through an existing tracheal tube, until the distal tip is at or near the tip of the tube. Oxygen for ventilation, suction or irrigation can also be applied in succession via, for example, quick fit connectors to the proximal end if desired. Once the anatomy is visualized, the light source, camera or eyepiece, and oxygen/suction/irrigation can all be disconnected from the proximal end of the subject device. The endotracheal tube can then be completely removed by sliding it out of the trachea, along, and off the proximal end of the subject device. The connectors of the subject device can be of a suitable diameter and located at different positions relative to the proximal end to permit their passage through the tracheal tube. The new tracheal tube can be loaded onto the subject device and the illumination and visualization equipment reconnected. The tracheal tube can be advanced down into the trachea while observing the airway anatomy via the subject device. Preferably, the subject device can be rigid enough to maintain its location in the trachea as it guides a replacement endotracheal tube into the trachea.

Alternatively, the image guide and illumination fiber(s) can remain connected until the endotracheal tube to be replaced has been slid out of the trachea. This allows continuous monitoring of the location of the distal tip of the tube exchanger, reducing the risk of the tube exchanger being dislodged during removal of the endotracheal tube. Once the tube is completely out of the patient, the proximal ends of the image guide and illumination fiber(s) can be disconnected to slide the tube off of the exchanger and slide a new tube onto the exchanger. The image guide and illumination fiber can then be reconnected to confirm the position of the exchanger before and during the placement of the new tube into the patient.

In order to utilize the subject invention during the exchange of an endotracheal tube, the fiber optic bundle can, preferably, be approximately the same length as a commercially available endotracheal tube exchanger, for example about 80–100 cm. In addition, referring to FIG. 3, markings can be provided on its wall indicating, for example in 5 cm increments, the length from its distal end to any given mark. This can allow the clinician to better gauge whether the distal tip is likely to be in the oropharynx, trachea, bronchus or beyond and can therefore improve patient safety.

EXAMPLE 4

Figure 3:
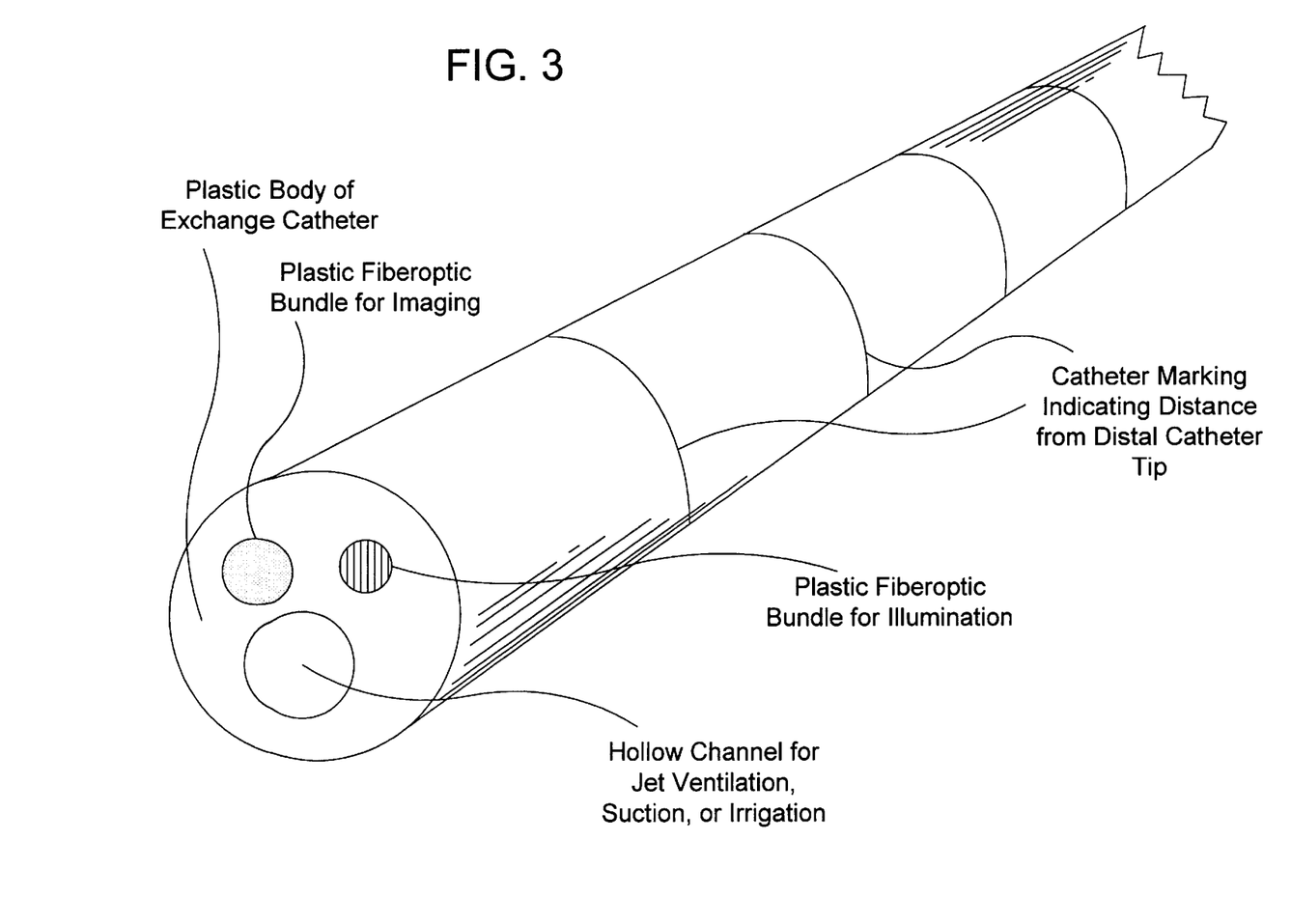
FIG. 3 illustrates markings and a hollow channel for ventilation, suction, and/or irrigation, in accordance with the subject invention.

Referring to FIG. 3, the subject invention, for example the devices disclosed in the previous examples, can have a hollow channel of sufficient caliber to provide adequate jet ventilation, suction and/or irrigation, if desired. Accordingly, if mucus plugs are visualized they can be suctioned and if secretions obstruct vision, the lens can be cleaned with irrigation through the hollow channel. Advantageously, ventilation can be provided through the hollow channel during the exchanging of endotracheal tubes.

The subject invention can also incorporate deflection, for example of about 0–60°, between about 1–10 cm from the distal tip, to allow a clinician to direct the subject device down either bronchus, towards a mucus plug, or away from the tracheal wall, simply by rotating the device along its length. This deflection may be incorporated into a device such that the distal tip of the subject scope conforms to the shape of an endotracheal tube while within the tube. When the distal end of the scope is advanced past the distal end of tube, the tip can assume a predefined deflection, for example due to memory in the stylet.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method of exchanging endotracheal tubes, said method comprising the steps of:
   (a) inserting an intubation scope, said intubation scope comprising an image guide, into an endotracheal tube to be replaced, wherein a proximal end of said intubation scope is connected to a viewing system to allow a user to view images of a patients airway;
   (b) completely withdrawing the endotracheal tube from the patient;
   (c) disconnecting the proximal end of said intubation scope from said viewing system;
   (d) withdrawing the preexisting endotracheal tube over the proximal end of said intubation scope;
   (e) loading a new endotracheal tube onto the proximal end of said intubation scope;
   (f) reconnecting the proximal end of said intubation scope to the viewing system; and
   (g) advancing the new endotracheal tube into its proper position while observing the anatomy of the airway through said image guide.

2. The method, according to claim 1, wherein said intubation scope further comprises a hollow channel which allows one or more of the following: ventilation, suction, injection, and irrigation.

3. The method, according to claim 1, wherein said intubation scope further comprises markings which indicate the distance from the distal end of said intubation scope to assist in estimating the location of the distal end of said intubation scope.

4. The method, according to claim 1, wherein said intubation scope further comprises a deflection at the distal end of said intubation scope to assist a user in the placement of said intubation scope.

* * * * *